(12) United States Patent
Saitoh et al.

(10) Patent No.: US 7,898,654 B2
(45) Date of Patent: Mar. 1, 2011

(54) EQUIPMENT AND METHOD FOR DETECTING FOREIGN MATTERS

(75) Inventors: Tatsuhiko Saitoh, Yokohama (JP); Yuji Kobayashi, Yokohama (JP); Takayuki Shimazu, Yokohama (JP)

(73) Assignee: Sumitomo Electric Industries, Ltd., Osaka-shi (JP)

( * ) Notice: Subject to any disclaimer, the term of this patent is extended or adjusted under 35 U.S.C. 154(b) by 89 days.

(21) Appl. No.: 12/504,834

(22) Filed: Jul. 17, 2009

(65) Prior Publication Data

US 2010/0020314 A1 Jan. 28, 2010

(30) Foreign Application Priority Data

Jul. 25, 2008 (JP) ............................. 2008-192606

(51) Int. Cl.
*G01N 21/00* (2006.01)
(52) U.S. Cl. ................................. 356/237.3; 356/237.1
(58) Field of Classification Search ............... 356/237.3
See application file for complete search history.

(56) References Cited

U.S. PATENT DOCUMENTS

| | | | | |
|---|---|---|---|---|
| 5,291,028 A | * | 3/1994 | Droge et al. ................. | 250/568 |
| 7,719,669 B2 | * | 5/2010 | Matsui et al. ............. | 356/237.1 |
| 2002/0135757 A1 | * | 9/2002 | Shires ....................... | 356/237.1 |
| 2008/0013084 A1 | | 1/2008 | Matsui et al. | |
| 2008/0024778 A1 | | 1/2008 | Honda et al. | |

FOREIGN PATENT DOCUMENTS

| | | | |
|---|---|---|---|
| JP | 6-323999 | | 11/1994 |
| JP | 9-287921 A | | 11/1997 |
| JP | 9-304294 | | 11/1997 |
| JP | 09287921 A | * | 11/1997 |
| JP | 2003-202297 | | 7/2003 |
| JP | 2004-301690 | | 10/2004 |
| JP | 2007-178407 A | | 7/2007 |
| JP | 2008-020359 A | | 1/2008 |

* cited by examiner

*Primary Examiner*—Roy Punnoose
(74) *Attorney, Agent, or Firm*—Venable LLP; Michael A. Sartori; Leigh D. Thelen (57) ABSTRACT

A foreign matter detector and a foreign matter detecting method are provided, with which foreign matter detection performance can be improved. The foreign matter detector comprises: a means for irradiating first inspection light and second inspection light to an inspection area such that their incident planes are perpendicular to each other; a measuring means for measuring the spectrum of reflected light, the reflected light being a reflection of the inspection light at the inspection area; and a means for determining, by analyzing the spectrum of the reflected light, whether any foreign matter is intermingled or not.

6 Claims, 10 Drawing Sheets

EQUIPMENT AND METHOD FOR DETECTING FOREIGN MATTERS

BACKGROUND OF THE INVENTION

1. Field of the Invention

The present invention relates to equipment and methods for detecting foreign matters, particularly fibrous foreign matters, intermingled with inspection objects.

2. Description of the Background Art

Japanese Patent Application Publication No. H9-304294 discloses a surface inspection apparatus and a surface inspection method using the apparatus. The disclosed equipment includes: a stand having a complementary color relative to the surface color of an inspection object, the stand being provided so as to be situated at the back of the inspection object; a lighting unit for lighting an inspection object; a color camera for photographing the inspection object; and a processor for perceiving a foreign matter by processing a picture photographed with the camera. Also, Japanese Patent Application Publication No. H6-323999 discloses a method of distinguishing a foreign matter from an inspection object by evaluating the results of operation made using a differential circuit, a difference circuit, a judgment circuit, etc. with respect to video signals obtained using a scanning-type imaging device. However, the performance of these equipment and methods has been insufficient for detecting a thin fibrous foreign matter.

SUMMARY OF THE INVENTION

An object of the present invention is to provide a foreign matter detector and a foreign matter detecting method, with which foreign matter detection performance can be improved.

A foreign matter detector according to the invention comprises: a means for irradiating inspection light to the inspection area of a stand on which inspection objects are placed; a measuring means for measuring the spectrum of the reflected light that is a reflection of the inspection light at the inspection area; and a means for determining, by analyzing the spectrum of the reflected light, whether any foreign matter is intermingled or not. In this foreign matter detector, the inspection light includes first inspection light and second inspection light, and their incident planes are perpendicular to each other.

Another aspect of the invention is a foreign matter detecting method comprising: a step of irradiating first inspection light and second inspection light to the inspection area of a stand having inspection objects placed thereon, such irradiation being done in a manner such that their incident planes are perpendicular to each other; a step of measuring the spectrum of reflected light of the first and second inspection light, the reflected light being a reflection caused at the inspection area; and a step of determining, by analyzing the spectrum of the reflected light, whether any foreign matter is intermingled or not.

When the inspection light is irradiated to an inspection object, the diffuse reflection light (scattered light of low intensity) that is irradiated in all directions and the regular reflection light (high strength) that is reflected only in a specific direction will return from the surface of the inspection object. In the foreign matter detector according to the present invention, the probability of capturing regular reflection light from a fibrous foreign matter is secured by providing a means with which the first inspection light and the second inspection light are irradiated to the inspection area so that their incident planes may be perpendicular to each other. Therefore, strong regular reflection light from a foreign matter surface can easily be delivered to a measuring means, and hence it is possible to improve the capability of detecting a fibrous foreign matter for which the quantity of diffuse reflection light is small.

The above-mentioned features and other features, aspects, and advantages of the present invention will be better understood through the following description, appended claims, and accompanying drawings. In the explanation of the drawings, an identical mark is applied to identical elements and an overlapping explanation will be omitted.

DETAILED DESCRIPTION OF THE INVENTION

In the following, preferred embodiments of the present invention will be explained in detail with reference to the accompanying drawings.

Embodiment 1

Figure 1:
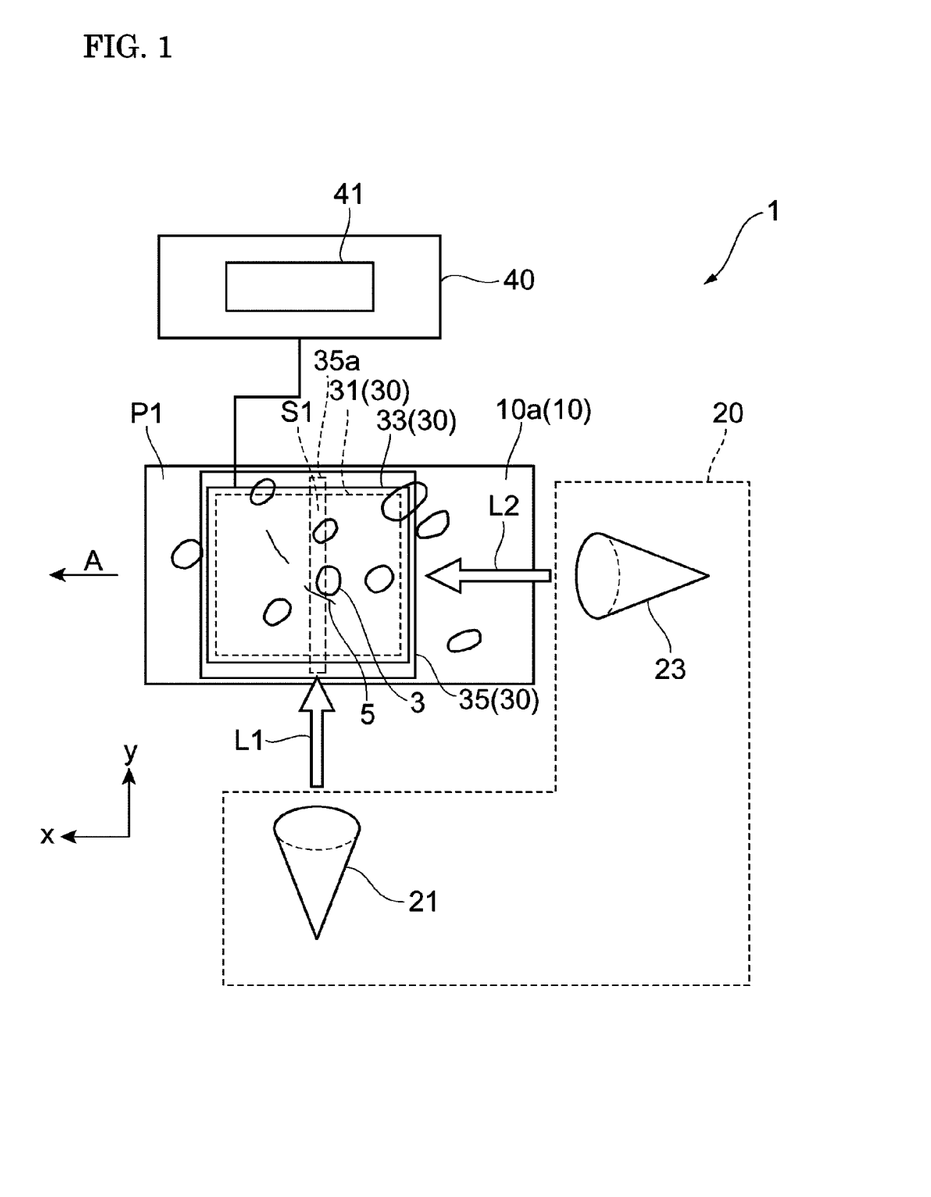
FIG. 1 is a conceptional schematic diagram of a foreign matter detector according to Embodiment 1 of the present invention.

FIG. 1 is a conceptional schematic diagram of a foreign matter detector 1 relating to Embodiment 1 of the present invention. A foreign matter detector 1 is equipped with a carrying unit (conveyor) 10, a lighting unit 20, a spectrum measuring unit 30, and a personal computer (PC) 40.

The carrying unit 10 is a means, more specifically a belt conveyor, for conveying inspection objects (e.g., beans) 3 with which fibrous foreign matters (e.g., a hair) 5 might be intermingled. The belt conveyor has a belt 10a, on the upper surface P1 of which inspection objects 3 are placed, and which is made of a material having low infrared reflectance. The inspection objects 3 placed on the belt 10a are conveyed in the direction A (the positive direction of the x-axis). The width of the belt 10a is preferably within a range to which the lighting unit 20, as mentioned later, can irradiate light and for which measurement with a below-mentioned camera 33 is possible.

The lighting unit 20 is composed of a first lighting unit 21 which outputs first inspection light L1 and a second lighting unit 23 which outputs second inspection light L2, the inspection light L1 and L2 are near infrared light having a central wavelength in a wavelength range of 900 nm to 2500 nm. The lighting unit 21 irradiates the inspection light L1 to an inspection area S1 such that the incident plane of the inspection light L1 and the moving direction A of the belt 10a are perpendicular to each other. The lighting unit 23 irradiates the inspection light L2 to the inspection area S1 such that the incident plane of the inspection light L2 and the moving direction A of the belt 10a lie in parallel with each other. Thus, the first inspection light L1 output from the first lighting units 21 and the second inspection light L2 output from the second lighting unit 23 have incident planes that are perpendicular to each other relative to the upper surface P1 of the belt 10a.

The spectrum measuring unit 30 is a means for measuring the spectrum of the reflected light that has been reflected from the inspection objects 3 according to the irradiation of the inspection light L1 and L2. The spectrum measuring unit 30 is composed of a camera 33, a slit 35, and a diffraction grating 31, the slit 35 and the diffraction grating 31 being provided at the foregoing part of the camera 33.

The slit 35, which has an opening portion 35a formed such that the longitudinal direction thereof extends in the y-axis direction, linearly defines the inspection area S1 where the spectrum is measured. Also, since the longitudinal direction of the opening portion 35a of the slit 35 and the incident plane of the second inspection light L2 are perpendicular to each other, the sensitivity of the camera 33 for receiving the reflected light that has been reflected at the surface of the fibrous foreign matters 5 is improved.

The reflected light that has been reflected from the inspection area S1 is split by the diffraction grating 31 in the x-axis direction according to the wavelength. The reflected light that has been split by the diffraction grating 31 is received by the two-dimensional light-receiving face of the camera 33. Thus, the reflected light that has been reflected from a given unit region in the inspection area S1 is split according to the wavelength and is input into each of the receiving sensors constituting the light-receiving face of the camera 33. In such case, the y-axis direction of the two-dimensional light-receiving face of the camera 33 corresponds to a position in the inspection area S1, and the x-axis direction corresponds to the split light wavelength.

The electric charge that occurs according to the reception of light by the two-dimensional light-receiving face of the camera 33 is digitally changed by an A/D converter so that digital data on the distribution of the light intensity is formed for every wavelength region. The digital data thus formed is transmitted through a cable to the PC 40 from the data output terminal of the camera 33. The PC 40 has a judging system (judging part) 41 in which the intensity distribution of the reflected light is data-processed and image-processed for every measured wavelength region. The judging system 41 judges whether or not any fibrous foreign matter 5 exists in the inspection area S1.

Figure 2:
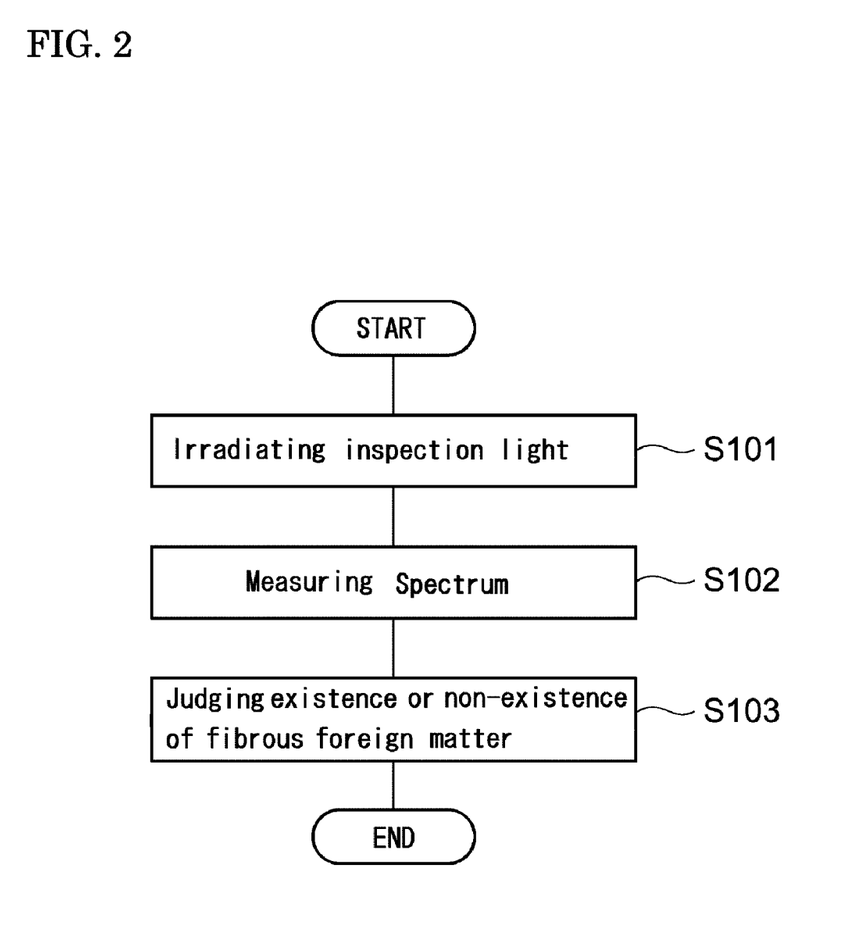
FIG. 2 is a flow chart showing the overall flow of foreign matter detection performed by the foreign matter detector of FIG. 1.

The following description is concerned about a method of using a foreign matter detector 1 for detecting a fibrous foreign matter 5 which intermingles with inspection objects 3. FIG. 2 is a flow chart showing the overall flow of the foreign matter detection. First, first inspection light L1 and second inspection light L2 are irradiated to an inspection area S1 such that their incident planes may be perpendicular to each other (S101 step). Next, the spectrum of reflected light that has been reflected from the inspection area S1 is measured (S102 step). Moreover, the existence or non-existence of fibrous foreign matters 5 is judged from the intensity distribution of the reflected light at a given wavelength region (S103 step).

In the S101 step, the belt conveyor 10 is operated beforehand at a pre-determined conveyance speed before the feed of inspection objects 3 onto the belt conveyor 10 is started. Then, the conveyance speed set for the belt conveyor 10 is set to a judging system 41 as a measuring condition data. Preferably, the conveyance speed of the belt conveyor 10 should be set within a range where the camera 33 can detect the inspection objects 3 sufficiently precisely. When the feed of the inspection objects 3 to the belt conveyor 10 is started, the lighting units 21 and 23 emit inspection light L1 and L2 respectively so as to irradiate the inspection area S1. The inspection area S1 is an area sufficient widthwise to cover the part where the inspection objects 3 are loaded on the belt 10a.

At the S102 step, the reflected light that has been reflected from the inspection area S1 is split by a diffraction grating 31 in the x-axis direction according to the wavelength and is received by the two-dimensional light-receiving face of the camera 33. At the light-receiving face, an electric charge occurs according to reception of light, and the electric charge thus generated is digitally converted by the A/D converter of the camera 33 so as to make a digital data on the distribution of the light intensity for each wavelength region. The digital data is transmitted in time-series through a cable from the data output terminal of the camera 33 to the PC 40.

At the S103 step, the judging system 41 of the PC 40 conducts judgment by a unit of pixel (one line unit on x-axis of the receiving sensor) of the inspection area S1. First, the part where the values of reflectance at a plurality of wavelengths are all below the pre-determined background threshold value is judged as the background, and a part other than such part is judged as the region excepting the background region, that is, as a "region to be identified" (i.e., an inspection object 3 or a fibrous foreign matter 5). Thereafter, the inspection objects 3 and the fibrous foreign matters 5 are distinguished by operating the values of reflectance for a plurality of wavelengths with respect to the identified region.

Figure 3A:
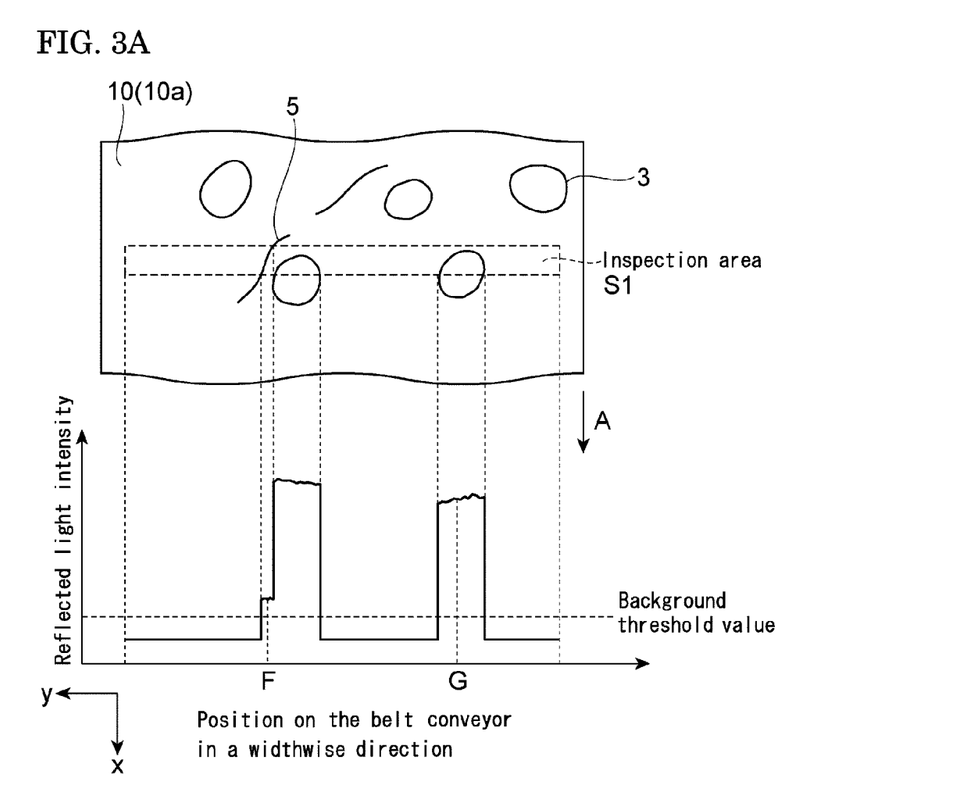
FIG. 3A is a diagram for illustrating the intensity distribution of the reflected light from the inspection area: the upper half of the diagram is a conceptional schematic diagram showing the inspection area as well as the inspection objects and fibrous foreign matters 5 passing there; the lower half is a graph showing the intensity distribution at a specific wavelength of the reflected light.
Figure 3B:
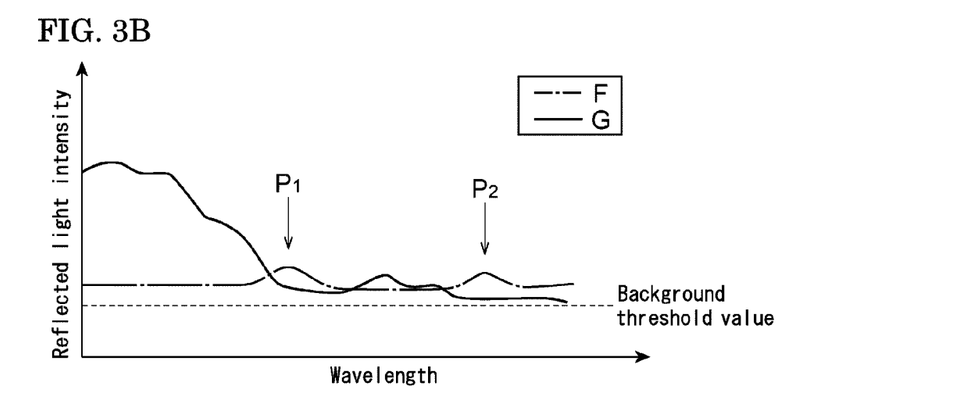
FIG. 3B is a graph showing the spectrum of reflected light at point F and point G of FIG. 3A.

There are various methods of operation to distinguish between an inspection object 3 and a fibrous foreign matter 5. FIG. 3A illustrates the intensity distribution of reflected light from the inspection area S1: the upper half of the figure is a conceptional schematic diagram showing the inspection area S1, as well as the inspection objects 3 and fibrous foreign matter 5 which are passing there; the lower half is a graph showing an intensity distribution at a specific wavelength of the reflected light. In the graph, the abscissa indicates a position on the belt conveyor in a widthwise direction thereof, and the ordinate shows a reflected light intensity. FIG. 3B is a graph showing the wavelength characteristics of reflected light (x-axis data of a light-receiving sensor) at points F and G of FIG. 3A, and the abscissa indicates a wavelength and the ordinate indicates the intensity of the reflected light. As shown in FIG. 3B, reflectance peaks P1 and P2, which are not seen for an inspection object 3, are recognized in the wavelength characteristics of reflected light at the F-point corresponding to a unit region in which a fibrous foreign matter 5 exists.

Focusing on this point, an algorithm for detecting the reflectance peaks P1 and P2 is incorporated beforehand in the judging system 41 of the foreign matter detector 1, such that, in a case where the reflectance peak P1 and reflectance peak P2 are detected at the same time, it is judged that a fibrous foreign matter 5 is detected in the pixel. In order to improve the detecting performance, the judging system 41 is designed so as to determine that a fibrous foreign matter 5 exists, only when a plurality of pixels in which a fibrous foreign matter 5 is judged to have been detected in a specific area. That is, when three or more pixels in which a fibrous foreign matter 5 is judged to have been detected exist altogether in 25 pixels of 5×5, for example, it is determined that a fibrous foreign matter 5 exists. This judgment method is just an example, and a more complicated judgment algorithm having high identifying performance may be incorporated in the judging system 41 included in a PC 40.

When inspection light is irradiated to inspection objects 3, diffuse reflection light (scattered light) and regular reflection light return from the surface. The diffuse reflection light is radiated to all directions from the surface of the inspection object 3, but the intensity of the light is weak. In a case where the surface area is narrow, as in the case of a fibrous foreign matter 5 such as a hair or the like, it would be difficult to detect a foreign matter by using the diffuse reflection light if the light quantity of the diffuse reflection light is feeble or scarce. As for the regular reflection light, although the intensity of the light is high, the angle range in which detection can be achieved is limited since the reflection occurs only in a specific direction where the incident angle and the reflection angle become equal with each other. Therefore, to detect a fibrous foreign matter 5 efficiently, it is necessary to capture the regular reflection light that is reflected only in the specific direction.

In the foreign matter detector 1 and the foreign matter detecting method using the same, first inspection light L1 and second inspection light L2 are irradiated by a lighting unit 20 such that their incident planes may be perpendicular to each other. Therefore, the information of high-intensity regular reflection light reflected at the surface of a fibrous foreign matter 5 can easily be transmitted to a spectrum measuring unit 30 and the foreign matter can be detected using the high-intensity regular reflection light. Accordingly, with the foreign matter detector 1, it is possible to improve the foreign matter detection performance.

Also, since the foreign matter detector 1 is equipped with the spectrum measuring unit 30 comprising of the diffraction grating 31 and the camera 33, the light that has been reflected from the inspection area S1 can be split by the diffraction grating 31, which is a means for splitting light, according to the wavelength, and the light intensity can be measured for every wavelength region of the split light. Consequently, identifying a foreign matter by the spectrum analysis becomes possible.

The incident plane of the second inspection light L2, which is irradiated to the inspection area S1, and the longitudinal direction of the slit 35, which is provided at the foregoing part of the diffraction grating 31, are perpendicular to each other. Therefore, it is possible to increase the value of opening to the reflected light which is a reflection of the second inspection light at the surface of a fibrous foreign matter 5, and hence the reflected light can efficiently be captured.

Figure 4:
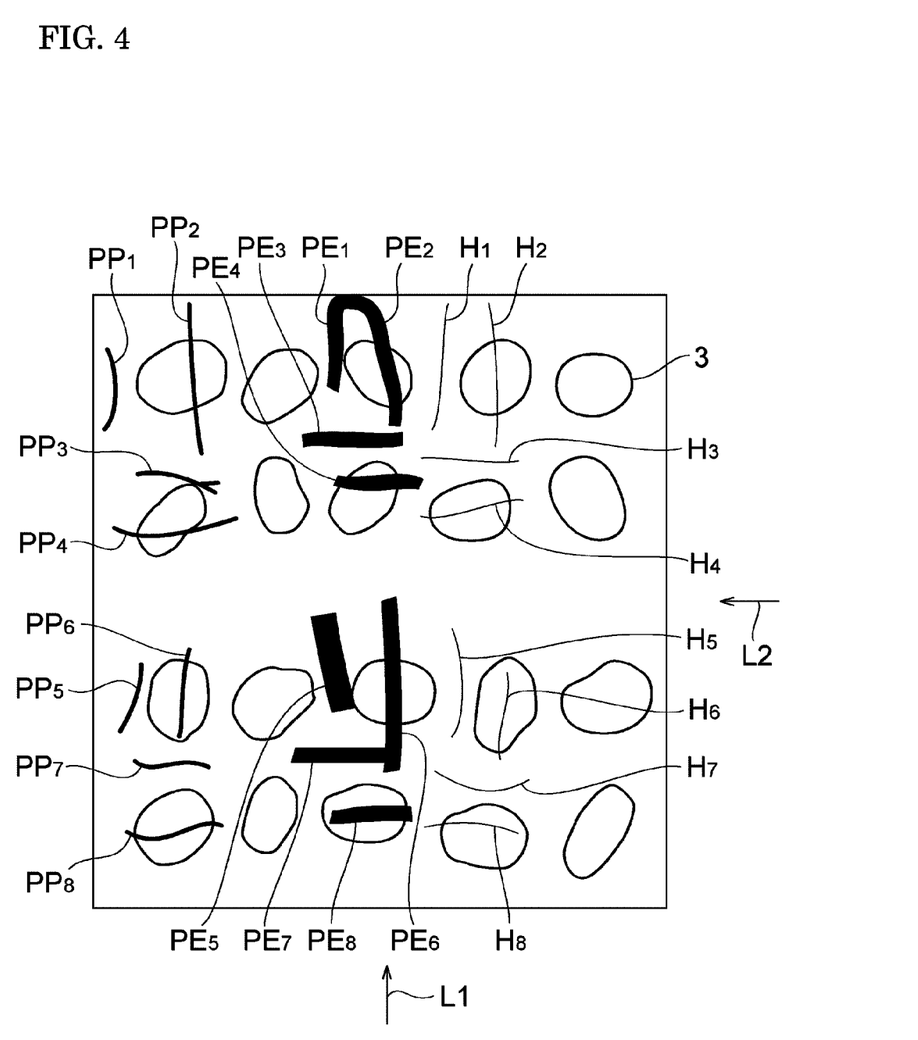
FIG. 4 is a front view showing an example of inspection area in which inspection objects are placed with fibrous foreign matters intermingled.

Hereinafter, the effect of the foreign matter detector 1 and the foreign matter detecting method using the same will be described with respect to actual examples. FIG. 4 is a front view showing an example of the inspection area S1 in which inspection objects 3 are placed, with fibrous foreign matters 5 intermingled. In the inspection area S1, the following things exist as fibrous foreign matters 5: eight pieces of polypropylene fibers $PP_1$ to $PP_8$, eight pieces of polyethylene fibers $PE_1$ to $PE_8$, and eight pieces of hairs $H_1$ to $H_8$.

Figure 5:
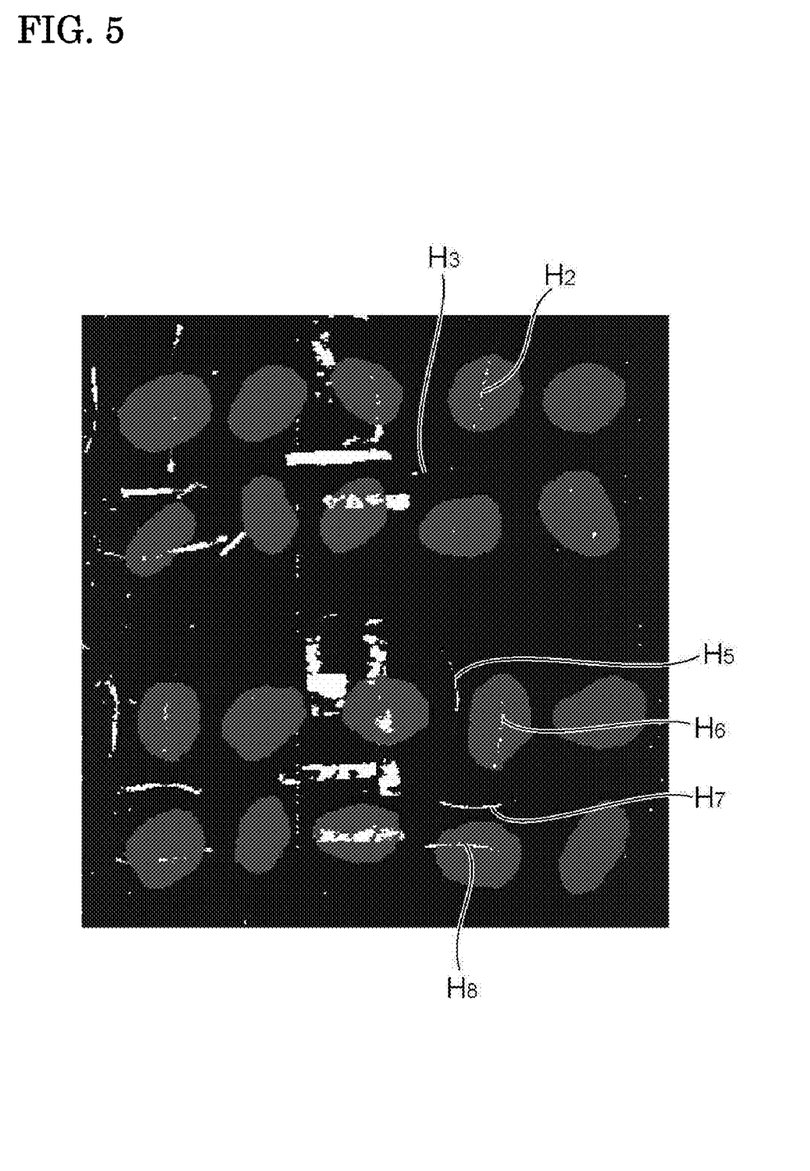
FIG. 5 is a photograph showing the intensity distribution in the case where inspection light L1 only is irradiated to the inspection area of FIG. 4.
Figure 6:
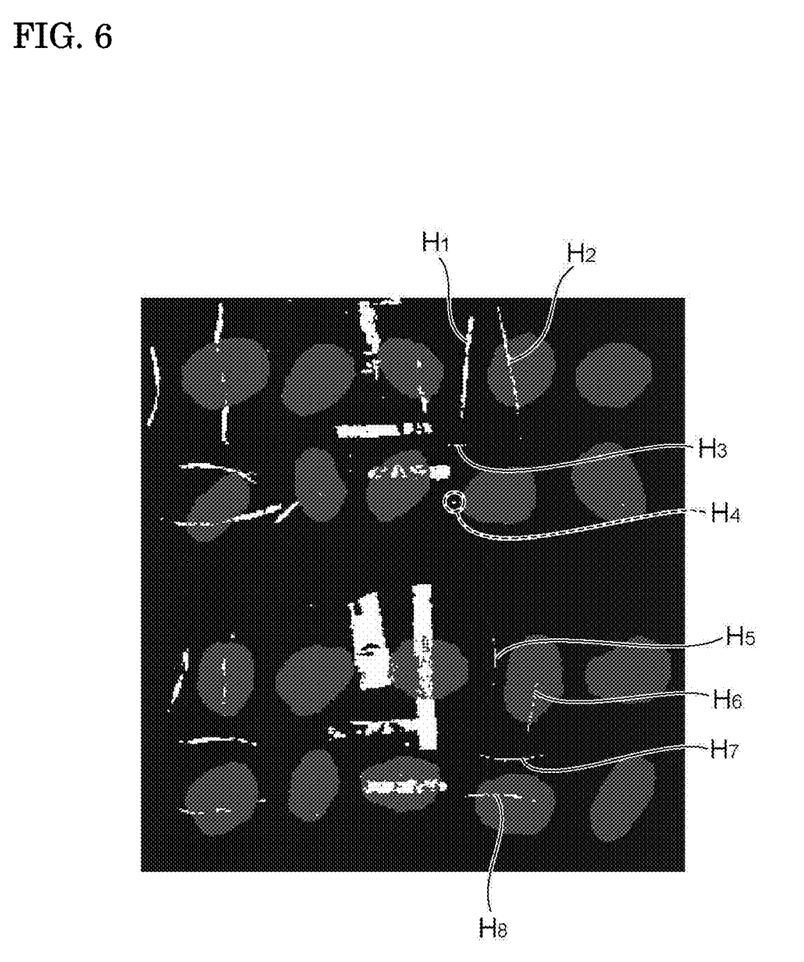
FIG. 6 is a photograph showing the intensity distribution in the case where beams of inspection light L1 and L2 are irradiated to the inspection area of FIG. 4.
Figure 7:
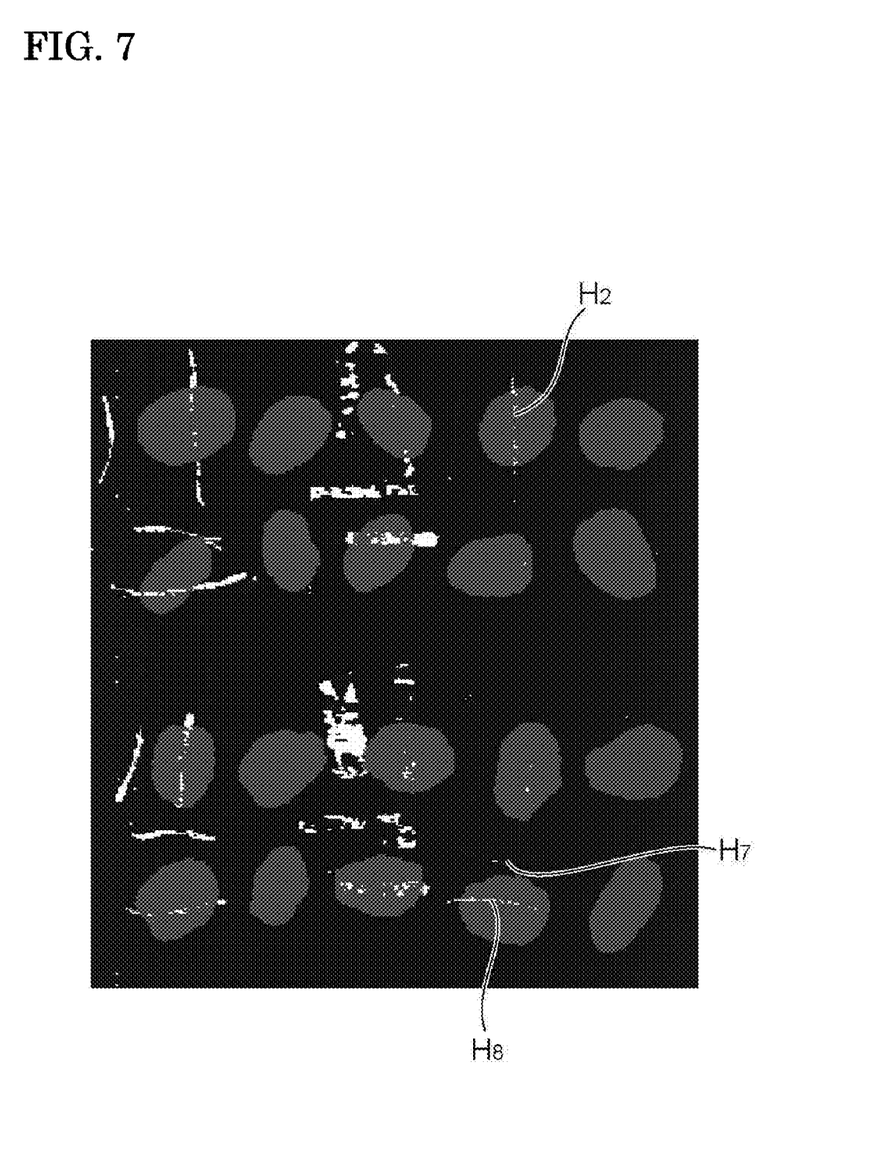
FIG. 7 is a photograph showing the intensity distribution in the case where three beams of inspection light including L1 and L2 are irradiated to the inspection area of FIG. 4.

FIGS. 5 to 7 are photographs each showing the intensity distribution obtained at a given wavelength based on the spectrum measured by the diffraction grating 31 and the camera 33 with respect to the inspection area S1: FIG. 5 is a case where only the inspection light L1 is irradiated; FIG. 6 is a case where two beams of the inspection light L1 and L2 are irradiated, and FIG. 7 is a case where three beams of inspection light including the inspection light L1 and L2 are irradiated. The polypropylene fibers $PP_1$ to $PP_8$ and polyethylene fibers $PE_1$ to $PE_8$, which are comparatively thick as compared with hairs $H_1$ to $H_8$, are all detected in any cases, and there are no great differences. However, in the detection of thin hairs $H_1$ to $H_8$, the results are different.

When only one beam of the inspection light L1 is irradiated (FIG. 5), six pieces ($H_2$, $H_3$, $H_5$, $H_6$, $H_7$, and $H_8$) are detected out of eight hairs $H_1$ to $H_8$. In the case where two beams of inspection light L1 and L2 are irradiated (FIG. 6), seven pieces ($H_1$, $H_2$, $H_3$, $H_5$, $H_6$, $H_7$, and $H_8$) are detected out of eight hairs $H_1$ to $H_8$, and the other hair $H_4$ is partially detected, although it is not judged as a foreign matter. As for the case where three beams of inspection light including inspection light L1 and L2 are irradiated, three pieces ($H_2$, $H_7$, and $H_8$) are detected out of eight hairs $H_1$ to $H_8$.

Figure 8:
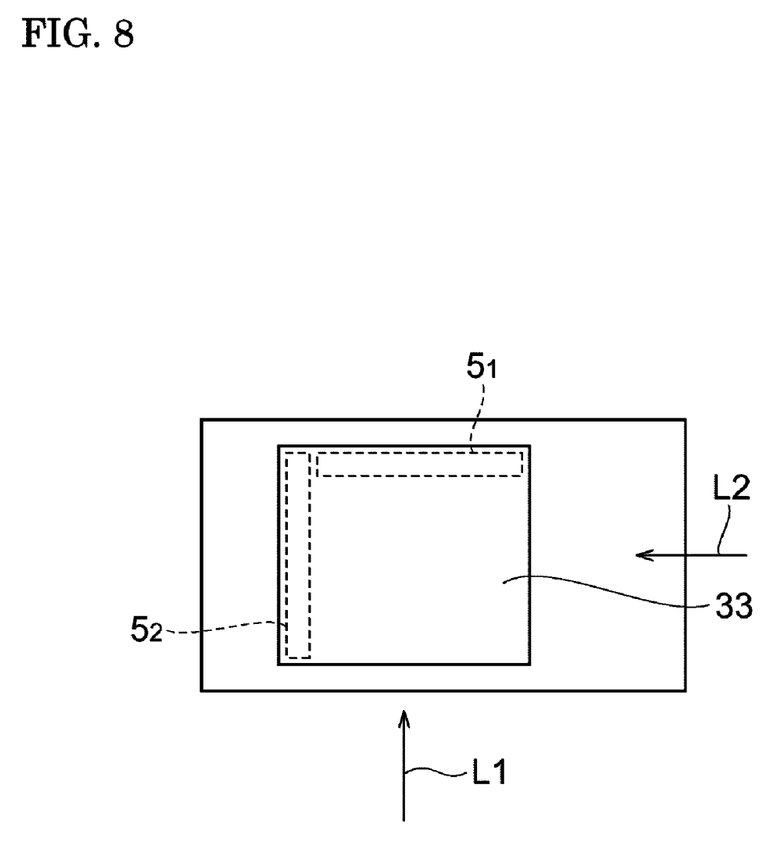
FIG. 8 is a conceptional schematic diagram showing the state in which beams of inspection light are irradiated to fibrous foreign matters.

The reason for such results can be explained as follows. FIG. 8 is a conceptional schematic diagram showing the state in which beams of inspection light L1 and L2 are irradiated to fibrous foreign matters $5_1$ and $5_2$. On the cylindrical surface of the fibrous foreign matter $5_1$, there exists a part having an angle which causes a regular reflection of the inspection light L1 to the camera 33. On the other hand, on the surface of the fibrous foreign matter $5_2$, the surface having the angle which causes a regular reflection of the inspection light L1 to the camera 33 hardly exists. Therefore, when only the inspection light L1 is used, it is easy to detect the fibrous foreign matter $5_1$ which easily return regular reflection light to the camera 33, but it is difficult to detect the fibrous foreign matter $5_2$ that cannot easily return the regular reflection light to the camera 33.

When the inspection light L2 is also irradiated under such conditions, the high-intensity regular reflection light that has occurred from the fibrous foreign matter $5_2$ is also easily delivered to the camera 33, so that the fibrous foreign matter $5_2$ is also easily detected, resulting in improvement of detection performance. On the other hand, when the three beams of inspection light including the inspection light L1 and L2 are irradiated, the light quantity of the regular reflection light from the fibrous foreign matters $5_1$ and $5_2$ becomes relatively weaker as compared to the inspection light, resulting in degradation of detection performance.

The more specific description is as follows. For measuring, standardization is done such that the quantity of reflected light from a white scattering board is defined as 100% and the light quantity in the case when the slit 35 is closed is defined as 0%. Thus, in the following explanation, the quantity of regular reflection light from the fibrous foreign matter 5 in the case where only the inspection light L1 is used is assumed to be 10% (10% at one light use) of the standardized value.

When a regular reflection occurs at a specific part of the fibrous foreign matter 5, the regular reflection light occurs from any one of a plurality of inspection light beams. The quantity of the regular reflection light which the fibrous foreign matter 5 returns to the camera 33 is "10% at one light use" in the case where the inspection light L1 and L2 are used at the same time, as well as in the case where only the inspection light L1 is used. However, when two beams of the inspection light L1 and L2 are used at the same time (at two light use), the total quantity of the inspection light irradiated to the inspection area S1 becomes twice the light quantity available in the case where only the inspection light L1 is used. In other words, "10% at one light use" becomes 5% at the two light use, resulting in degradation of the relative strength of the regular reflection light from the fibrous foreign matter 5.

Therefore, the detection sensitivity of the camera 33 with respect to the fibrous foreign matter $5_1$ is relatively degraded in the case where the inspection light L1 and L2 are used at the same time, as compared with the case where only the inspection light L1 is used. However, by using two beams of the inspection light L1 and L2 at the same time, it is made possible to detect the fibrous foreign matter $5_2$ that is located at an angle at which it is difficult to see when the inspection light L1 alone is used. Consequently, since the effect of such expansion of detection range exceeds the relative degradation of the regular reflection light, the performance of detecting a fibrous foreign matter improves in the case where the inspection light L1 and L2 are used at the same time.

When three lights are used, adding one light to the lights of the inspection light L1 and L2, the demerit of relative degradation of the regular reflection light from the foreign matter exceeds the merit of the expansion effect in the detection range, resulting in the decrease of performance of detecting a fibrous foreign matter. Therefore, from the viewpoint of fully utilizing the effect of expansion of the detecting range and minimizing the degradation of the regular reflection light from the foreign matter, it is effective to use two beams of the inspection light whose incident planes are perpendicular to each other. Thus, the performance of the foreign matter detector 1 to detect the fibrous foreign matter 5 can be improved.

Figure 9:
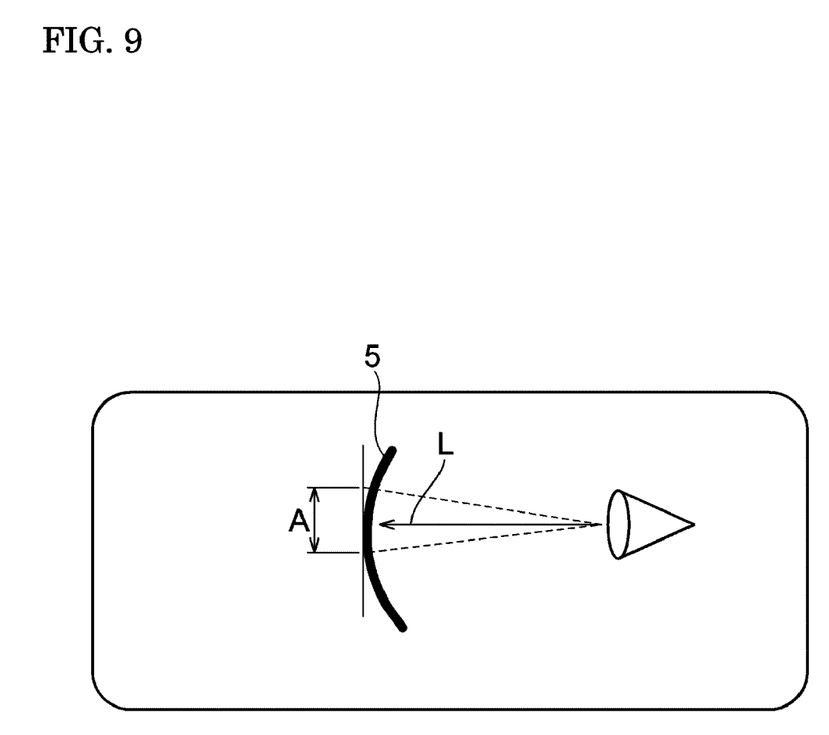
FIG. 9 is a conceptional schematic diagram showing the relationship between a fibrous foreign matter and inspection light.

As shown in FIG. 9, if the fibrous foreign matter 5 is arranged, not at an angle such that it is perpendicular to the incident plane of the inspection light L, but at an angle close to it (range A in the fibrous foreign matter 5), the probability of the regular reflection light being transmitted to the camera 33 will increase, depending on the surface texture of the fibrous foreign matter 5. Also, it is possible to remove the fibrous foreign matter 5 if the whole of it is not judged to be a foreign matter, but if the part of it is judged as a fibrous foreign matter 5.

In addition, when two beams of detection light are irradiated, it is possible to prevent misdetection, which might be caused by a flaw in the background board of a belt 10a, or the like. More specifically, if any flaw exists in the belt 10a, which is the background board, particularly in the case where the flaw is such that it delivers regular reflection light to the camera 33, the belt 10a would be judged as a fibrous foreign matter. However, irradiating two inspection light beams makes it possible to decrease the relative strength of the regular reflection light, and accordingly the misdetection power can be lessened.

Also, by providing a conveying means for conveying inspection objects, the irradiation of inspection light, the measurement of spectrum of the reflected light, and the judgment of foreign matter can be performed while the inspection objects are being conveyed, and it is easy to automate the foreign matter detection operation.

Embodiment 2

Figure 10:
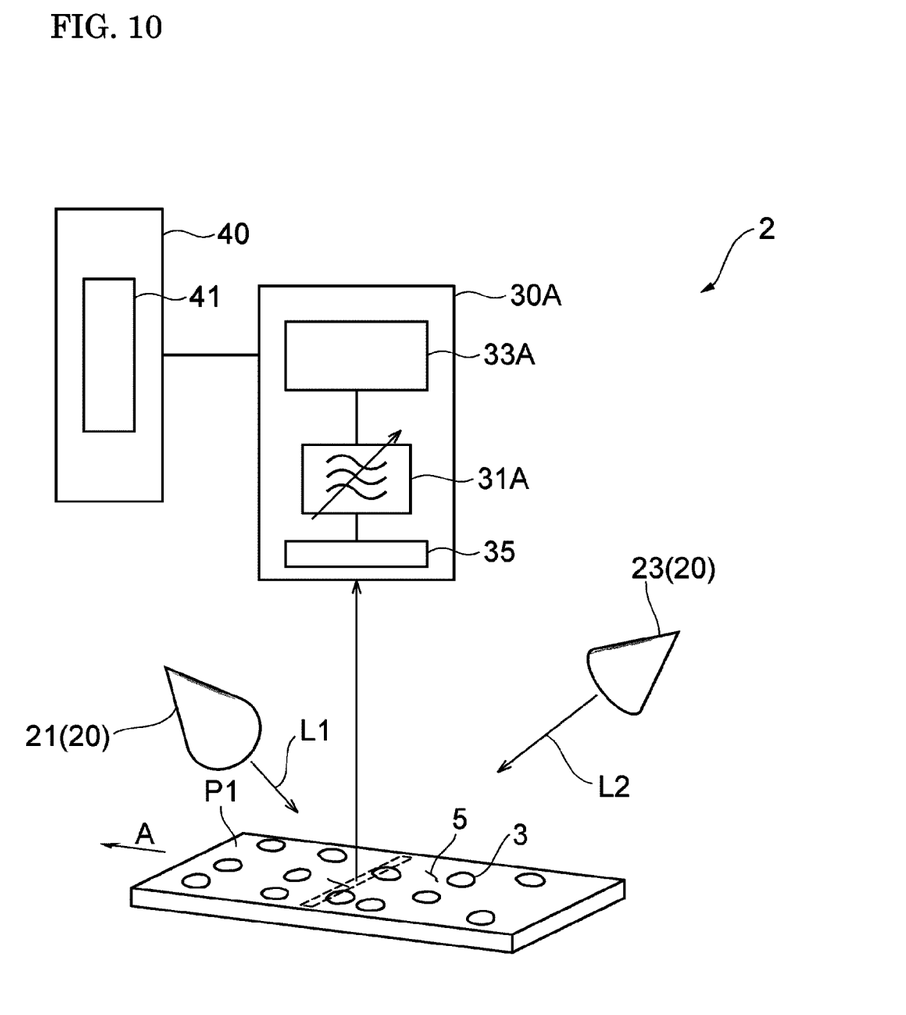
FIG. 10 is a conceptional schematic diagram of the foreign matter detector relating to Embodiment 2 of the present invention.

FIG. 10 is a conceptional schematic diagram of a foreign matter detector 2 relating to Embodiment 2 of the present invention. The foreign matter detector 2 differs from the foreign matter detector 1: that is, the former is equipped with a spectrum measuring unit 30A in place of the spectrum measuring unit 30. The spectrum measuring unit 30A is composed of a camera 33A, a slit 35, and a wavelength variable filter 31A: the camera 33A has two-dimensional light-receiving face consisting of area sensors; the slit 35 and the filter 31A are arranged at the foregoing part of the camera 33A.

With the wavelength variable filter 31A, the reflected light having pre-determined transmittable wavelength band can be selected out of the reflected light that has been reflected from the inspection area S1, and the so-selected reflected light is allowed to pass therethrough so as to be put out, and the reflected light having the other wavelength bands is caused to be attenuated. The pre-determined transmittable wavelength band can be altered. For example, the wavelength variable filter may be a mechanical filter which can change the wavelength by moving the filter material mechanically or may be an electric filter which alters the wavelength using the electric characteristics of its component. An example of the electric filter is a liquid crystal wavelength variable filter. The reflected light which has been output through the wavelength variable filter 31A is received by the two-dimensional light-receiving face consisting of area sensors. The camera 33A performs digital conversion with the A/D converter for the electric charge which occurs according to the reception by the two-dimensional light-receiving face, so that a transmittable wavelength band digital data on the distribution of the light intensity is formed.

The foreign matter detector 2 can exhibit the following effect in addition to achieving a similar effect like the foreign matter inspection apparatus 1 by measuring the intensity distribution of a plurality of needed wavelengths with the wavelength variable filter 31A. That is, in the foreign matter detector 2, only the wavelength data that is necessary for finding a foreign matter can be adopted by means of the wavelength variable filter 31A, and therefore the time required for such finding can be reduced, thereby the efficiency of the foreign matter detection can be enhanced (In the foreign matter detector 1, all wavelength data including the wavelength data which is unnecessary for finding the foreign matter are adopted). Also, a plurality of foreign matters having different reflection characteristics can easily be detected without exchanging a filter. Moreover, the detection wavelength can easily be adjusted according to the reflection characteristics of a foreign matter.

While this invention has been described in connection with what are presently considered to be the most practical and preferred embodiments, the invention is not limited to those embodiments, but on the contrary, is intended to cover various modifications and equivalent arrangements included within the spirit and scope of the appended claims. For example, a diffraction grating 31 is used as the means for splitting light in the foreign matter detector 1; however it is not limited to the diffraction grating, and a prism may be used instead. Also, in the present embodiment, a belt conveyor is used as a carrying unit 10; however, it may be a turntable.

The entire disclosure of Japanese Patent Application No. 2008-192606 filed on Jul. 25, 2008 including specification, claims drawings and summary are incorporated herein by reference in its entirety.

What is claimed is:

1. A foreign matter detector comprising:
   a means for irradiating first inspection light and second inspection light to an inspection area of a stand having inspection objects placed thereon, the incident planes of the first and second inspection light being perpendicular to each other;
   a measuring means for measuring the spectrum of reflected light, the reflected light being reflection of the first and second inspection light from the inspection area; and
   a means for determining, by analyzing the spectrum of the reflected light, whether any foreign matter is intermingled or not.

2. A foreign matter detector according to claim 1, wherein the measuring means comprises:
   a slit having an opening portion, the inspection area being defined linearly by the opening portion;
   a light splitting means for splitting, out of the reflected light, the light having passed through the slit according to wavelength; and
   a receiving means having a two-dimensional light-receiving face consisting of a plurality of receiving sensors, the light split by the light splitting means being received by the light-receiving face.

3. A foreign matter detector according to claim 1, wherein the measuring means comprises an optical filter and a light-receiving means, and wherein
   the optical filter selects, out of the reflected light, light having a pre-determined transmittable wavelength band and allows the selected light to pass therethrough, the pre-determined transmittable wavelength band being changeable, and wherein
   the receiving means has a two-dimensional light-receiving face and receives the light having passed through the optical filter.

4. A foreign matter detector according to claim 2, wherein the incident plane of the first inspection light irradiated to the inspection area and the longitudinal direction of the opening portion of the slit are perpendicular to each other.

5. A foreign matter detector according to claim 4, further comprising a conveying means for conveying inspection objects.

6. A foreign matter detecting method comprising:
   a step of irradiating first inspection light and second inspection light to the inspection area of a stand having inspection objects placed thereon, the incident planes of the first and second inspection light being perpendicular to each other;
   a step of measuring the spectrum of reflected light of the first and second inspection light, the reflected light being a reflection caused at the inspection area; and
   a step of determining, by analyzing the spectrum of the reflected light, whether any foreign matter is intermingled or not.

* * * * *